United States Patent
Wu

(10) Patent No.: US 9,980,979 B2
(45) Date of Patent: *May 29, 2018

(54) COMPOUNDS AND METHODS FOR ENHANCING ERYTHROPOIESIS

(71) Applicant: NATIONAL YANG-MING UNIVERSITY, Taipei (TW)

(72) Inventor: Rong-Tsun Wu, Taipei (TW)

(73) Assignee: NATIONAL YANG-MING UNIVERSITY, Taipei (TW)

( * ) Notice: Subject to any disclaimer, the term of this patent is extended or adjusted under 35 U.S.C. 154(b) by 56 days.

This patent is subject to a terminal disclaimer.

(21) Appl. No.: 14/980,264

(22) Filed: Dec. 28, 2015

(65) Prior Publication Data

US 2016/0106769 A1 Apr. 21, 2016

Related U.S. Application Data

(60) Division of application No. 13/930,849, filed on Jun. 28, 2013, now Pat. No. 9,248,143, which is a continuation of application No. 12/343,922, filed on Dec. 24, 2008, now abandoned.

(51) Int. Cl.
*A61K 31/7034* (2006.01)
*C07H 15/203* (2006.01)

(52) U.S. Cl.
CPC ....... *A61K 31/7034* (2013.01); *C07H 15/203* (2013.01)

(58) Field of Classification Search
None
See application file for complete search history.

(56) References Cited

U.S. PATENT DOCUMENTS

| 8,168,236 | B2 | 5/2012 | Wu |
| 9,089,585 | B2 * | 7/2015 | Wu ..................... A61K 36/704 |
| 2005/0042314 | A1 | 2/2005 | Wu |
| 2009/0074896 | A1 | 3/2009 | Wu |
| 2009/0092697 | A1 | 4/2009 | Wu |
| 2010/0160243 | A1 | 6/2010 | Wu |

FOREIGN PATENT DOCUMENTS

| CN | 101095894 | * | 1/2008 | ......... A61K 36/9066 |

OTHER PUBLICATIONS

Kwon et al., "Farnesyl Protein Transferase Inhibitory Components of Polygonum multiflorum" Arch Pharm Res (2009) vol. 32 No. 4 pp. 495-499.*
English machine translation of CN101095894 (Published Jan. 2008) downloaded from translationportal.epo.org.*
Chong et al., "Erythropoietin Requires NF-kB and its Nuclear Translocation to Prevent Early and Late Apoptotic Neuronal Injury During Amyloid Toxicity," Current Neurovascular Research (2005) vol. 2, No. 5, pp. 387-399.
Guan S. et al., "A potent tyrosinase activator from Radix Polygoni multiflori and its Melanogenesis stimulatory effect in 816 melanoma cells," Phytother Res. 2008. 22(5): 660-663.
Hayat et al., "Erythropoietin stimulating agents in the management of anemia chronic kidney disease," Patient Preference and Adherence (2008) vol. 2, pp. 195-200.
Juul et al., "Epo and other hematopoietic factors," Seminars in Fetal and Neonatal Medicine (2007) vol. 12, pp. 250-258.
Kim et al., "A New Stilbene Glucoside Gallate from the Roots of Polygonum Multiflorum," Arch Pharm Res (2008) vol. 31, No. 10, pp. 1225-1229.
Kimura et al., "Effects of Stilbene Components of Roots of *Polygonum* ssp. on Liver Injury in Peroxidized Oil-Fed Rats," Planta Medica (1983) vol. 49, pp. 51-54.
Liu QL, et al., "Effect of 2, 3, 5, 4'-tetrahydroxystilbene-2-O-beta-D-glucoside on lipoprotein oxidation and proliferation of coronary arterial smooth cells," J. Asian Nat Prod Res. 2007. 9(6-8): pp. 689-697.
Matsumoto et al., "Hepatocyte growth factor: Renotropic role and potential therapeutics for renal disease," Kidney International (2001) vol. 59, pp. 2023-2038.
Wang R., et al., "Changes in hippocampal synapses and learning-memory ability in age-increasing rats and effects of tetrahydroxystilbene glucoside in aged rats," Neuroscience. 2007. 149 4: pp. 739-746.
Wang X, et al., "Protective effects of 2, 3, 5, 4'-tetrahydroxystilbene-2-O-beta-d-glucoside, active component of Polygonum multiflorum Thunb, on experimental colitis in mice," Eur J Pharmacal. 2008. 578(2-3): pp. 339-348.
Yazihan et al., "Erythropoietin attenuates hydrogen peroxide-induced damage of hepatocytes," Turk J. Gastroenterol (2007) vol. 18, No. 4, pp. 239-244.
Zhang Yz, et al., "Inhibitory effects of 2, 3, 5, 4'-tetrahydroxystilbene-2-O-beta-D-glucoside on experimental inflammation and cyclooxygenase 2 activity," J Asian Nat Prod Res. 2007. 9(3-5): pp. 355-363.

* cited by examiner

*Primary Examiner* — Eric Olson
(74) *Attorney, Agent, or Firm* — Birch, Stewart, Kolasch & Birch, LLP

(57) ABSTRACT

Compounds and methods for enhancing erythropoiesis. The compound contains a chemical structure of the formula (I) indicated below, in which R is a glucosyl group. In addition to having an erythropoiesis effect, the compound of the formula (I) is effective in enhancing erythropoietin formation, and increasing kidney function and expression of hepatocyte growth factor. The method includes the step of administering an effective amount of the compound of the formula (I) to a subject in need thereof and thereby results in an enhancement of erythropoiesis.

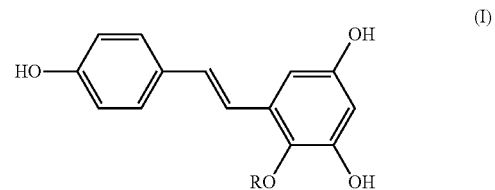

(I)

3 Claims, 6 Drawing Sheets

COMPOUNDS AND METHODS FOR ENHANCING ERYTHROPOIESIS

CROSS REFERENCE TO RELATED APPLICATIONS

This application is a Divisional of U.S. application Ser. No. 13/930,849, which is a Continuation of U.S. application Ser. No. 12/343,922, filed Dec. 24, 2008, pending. The entire contents of the aforementioned patent application are incorporated herein by this reference.

The instant application contains a Sequence Listing which has been submitted in ASCII format via EFS-Web and is hereby incorporated by reference in its entirety. Said ASCII copy, created on Aug. 11, 2013, is named 86522CON_ST25.txt and is 4,096 bytes in size.

FIELD OF THE INVENTION

The present invention relates generally to erythropoiesis, and more specifically to enhancement of erythropoiesis.

BACKGROUND OF THE INVENTION

Chronic kidney disease (CKD) is a worldwide public health problem, with adverse outcomes of kidney failure, cardiovascular disease and premature death (Levey, 2005). Patients with CKD are at high risks for progression to the end stage renal disease and need the dialysis or kidney transplantation to maintain a long-term survival. Anemia, an early symptom of CKD, results from underproduction of endogenous erythropoietin (Epo) by kidney (Zarzecki et al., 2004). In addition to CKD, anemia is also associated with other diseases, such as cancer, acute and chronic infections, autoimmune, inflammation and chronic rejection after solid-organ transplantation (Weiss and Goodnough, 2005).

Epo is a glycoprotein hormone mainly produced in adult kidney and fetal liver. Epo exerts its effect by binding to erythropoietin receptor (Epo receptor) on cell surface. When cells sense a relatively low oxygen level (such as the hypoxia), Epo is produced and released to regulate proliferation, differentiation, maturation, and survival in erythroid lineage cells (Moritz et al., 1997 and Fisher, 2003). Abnormal Epo levels in bloodstream may be an indicator for bone marrow and renal diseases. Relatively low Epo levels have been seen in patients with CKD, primary polycythemia rubra vera and chemotherapy-induced anemia. Relatively high Epo levels have been seen in secondary polycythemia and renal cancer patients (Eckardt and Kurtz, 2005 and Hodges et al., 2007).

Besides being produced in kidney and liver tissues, Epo and its receptors have been found in non-erythroid tissues and organs, including brain, eye, heart, lung, gut, pancreas, muscle, uterus and gonads (Eckardt and Kurtz, 1992). Epo-Epo receptor signaling contributes to wound healing responses, angiogenesis and local tissue-protective functions, such as neuroprotections, cardiovascular protections and protections from tissue ischemia and ischemia/reperfusion injury (Paschos et al., 2008 and Arcasoy, 2008). It has been reported that Epo has renoprotective effects by reducing the extent of renal dysfunction and facilitating the recovery from cisplatin-induced acute renal failure (Sepodes et al., 2006 and Arcasoy, 2008).

Erythropoiesis-stimulating agents (ESAs) are recommended by the National Kidney Foundation Kidney Disease Outcomes Quality Initiative guidelines to treat anemia of CKD in patients with treatment-responsive anemia. Recombinant human Epo (rHuEpo) has been approved for treating anemia of CKD, anemia in cancer patients receiving chemotherapy, for reducing transfusion requirements during surgery and for treating anemia in zidovudine-treated patients infected with the human immunodeficiency virus. A novel erythropoiesis stimulating protein (NESP), designed from Epo with a longer plasma half-life, has been approved for treating anemia in chronic renal failure (Fisher, 2003). It has been recommended that intravenous (i.v.) or subcutaneous (s.c.) administration of NESP be more than once per week for maintenance therapy. The pain, inconvenience due to frequent injection, and the development of anti-Epo antibodies because of inherent antigenicity associated with rHuEpo are of a great concerned (Bunn, 2007). Moreover, ESAs pose safety risks in patients with higher hemoglobin levels and may cause complications such as hypertension, thromboembolism, iron deficiency and severe pure red-cell aplasia (Wish and Coyne, 2007).

Therefore, a heretofore unaddressed need exists in the art to address the aforementioned deficiencies and inadequacies, especially in connection with erythropoiesis and kidney functions.

SUMMARY OF THE INVENTION

In one aspect, the invention is related to a method for enhancing erythropoietin formation in a subject in need thereof. The method includes administering to the subject an effective amount of a compound of the formula:

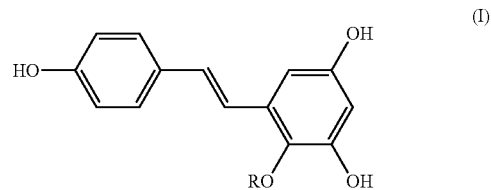

wherein R is a glycosyl group.

The glycosyl group is at least one selected from the group consisting of dihydroxyacetone, glucose, galactose, glyceraldehydes, threose, xylose, mannose, ribose, ribulose, xylulose, tagatose, psicose (allulose), fructose, sorbose, rhamnose, erythrose, erythrulose, arabinose, lyxose, allose, altrose, gulose, idose and talose and any combinations thereof.

In another aspect, the invention is related to a method for treating a disease and/or disorder in a subject that would benefit from erythropoietin treatment. The method includes administering to the subject an effective amount of the aforementioned compound of the formula (I).

The disease is at least one selected from anemia, a renal failure, and erythropoiesis deficiency-related diseases.

The disorder would benefit from an erythropoietin-related protective effect.

The erythropoietin-related protective effect is at least one selected from neuroprotection, cardiovascular protection, renoprotective effect, and protections from tissue ischemia and ischemia/reperfusion injury.

In another aspect, the invention is related to a method for enhancing erythropoiesis in a subject in need thereof. The method includes administering to the subject an effective amount of the aforementioned compound of the formula (I).

Further in another aspect, the invention is related to a method for enhancing kidney function in a subject in need thereof. The method includes administering to the subject an effective amount of the aforementioned compound of the formula (I).

Yet in another aspect, the invention is related to a method for increasing the expression of hepatocyte growth factor in a subject in need thereof. The method includes administering to the subject an effective amount of the aforementioned compound of the formula (I).

In another aspect, the invention is related to a method for treating a disease and/or disorder in a subject that would benefit from hepatocyte growth factor treatment. The method includes administering to the subject an effective amount of the aforementioned compound of the formula (I).

Further in another aspect, the invention is related to a method for treating a disease and/or disorder via regulating the expression of hepatocyte growth factor in a subject in need thereof. The method includes administering to the subject an effective amount of the aforementioned compound of the formula (I). The disease and/or disorder is at least one selected from allergic inflammation, osteoarthritis, rheumatoid arthritis, muscular dystrophy, muscular atrophy, skin ulcer, burn, scleroderma, crush syndrome, cerebrovascular diseases such as transient ischemic attack and stroke, neurodegenerative diseases such as amyotrophic lateral sclerosis, Alzheimer's disease and, Parkinson's disease, spinal cord injury, diabetic retinopathy, peripheral neuropathy, spinal canal stenosis, deafness, acute hepatitis, liver cirrhosis, fulminant hepatitis, fatty liver, surgical treatments for liver transplantation, partial resection and ischemia, kidney fibrosis, acute renal failure, chronic renal failure such as nephritic syndrome and obstructive nephropathy, surgical treatments for renal transplantation and ischemia, diabetic nephropathy, acute pneumonia, pulmonary fibrosis, surgical treatments for lung transplantation, partial resection and ischemia, inflammation-mediated heart diseases such as cardiac allograft rejection and myocarditis, cardiovascular diseases such as angina, cardiac infarction, cardiomyopathy and atherosclerosis obliterans, intestinal mucosal injury, inflammatory bowel disease, gastric ulcer or diabetes mellitus.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

Definitions

Figure 1:
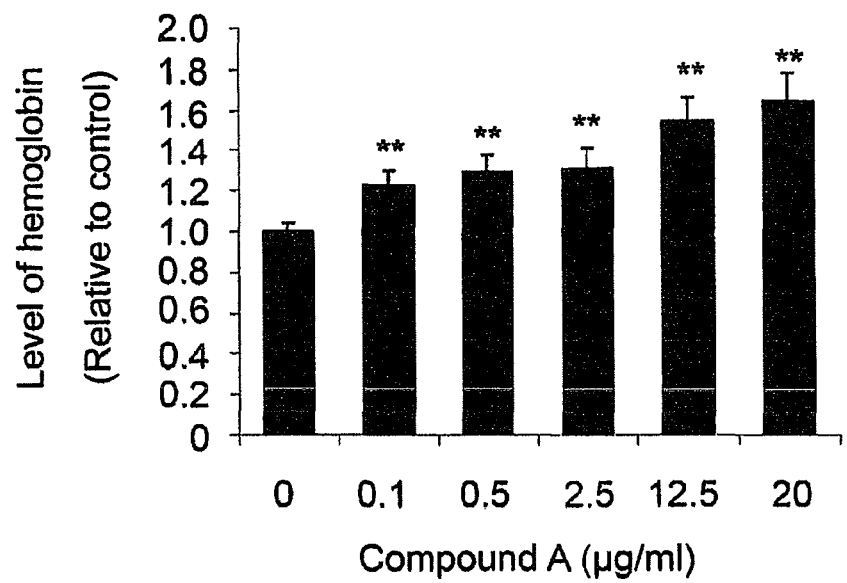
FIG. 1 is a graph showing Compound A enhances hemoglobin levels in bone marrow cells.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1

Purification of Compound A

Two kilograms of dry *Polygonum multiflorum* were ground in a pulverizer and the ground material was immersed in 2 liters of 85% (v/v) ethanol overnight to form a reaction solution. The reaction solution was collected, and another 2 liters of 85% (v/v) ethanol were added to the ground *Polygonum multiflorum* residue for further extraction according to the aforementioned procedure. The ethanol extraction was repeated for additional three times. The collected solution was filtrated using a gas-extracting apparatus (with Whatman #1 filter papers), and followed by concentration in a rotavapor (Buchi) at 40° C. to a six-fold reduction in volume. The concentrated filtrates were pooled together and partitioned 5 times with n-hexane/$H_2O$=1:1 (total 5 liters). The aqueous phase was collected and further partitioned 6 times with ethyl acetate water, EtOAc/$H_2O$=1:1 (total 6.5 liters), to obtain EtOAc layer. Six EtOAc layers were pooled together, concentrated, and the concentrate was dried in Freeze Dryer (Kingmech, Taiwan) to obtain the EtOAc extract (called "PoMuEPe"). The PoMuEPe was chromatographed on a Diaion® HP-200 column (4.8×60 cm; Mitsubishi Chemical) with a Methanol:$H_2O$=50:50 solvent system at a flow rate of 2 ml/min. Fractions were collected, dried and assayed for the ability to enhance hemoglobin formation. Fractions exhibiting activities were collected and called PoMuEPeD9. PoMuEPeD9 was chromatographed on a Sephadex™ LH20 column (2.6×100 cm; GE Healthcare Life Science) with a Methanol:$H_2O$=100:0 solvent system at a flow rate of 1 ml/min. Fractions were collected and assayed for their abilities in enhancing hemoglobin formation. Fractions showing bioactivity were collected and called PoMuEPeD9L11.

The chemical structure of the major component in PoMuEPeD9L11 was determined by nuclear magnetic resonance (NMR) spectroscopy (Bruker) and liquid chromatography/Mass spectrometry (LC/MS; Bruker). It was identified that the major component was 2,3,5,4'-tetrahydroxystilbene 2-O-β-D-glucopyranoside, called "Compound A," having the formula:

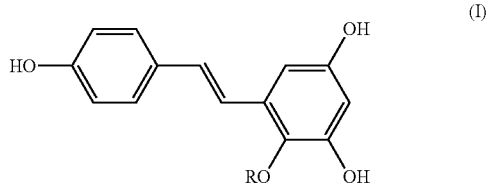

(I)

wherein R is a glucosyl group.

Example 2

Compound A Enhances Hemoglobin Formation

C57BL/6JNarl mice, 8-10 weeks of age, were purchased from the National Laboratory Animal Center (NLAC, Taiwan). Acute hemolytic anemia was induced by a single intraperitoneal (i.p.) injection of phenylhydrazine hydrochloride (Sigma-Aldrich) at a dose of 100 mg/kg in a phosphate buffered saline (PBS). Six days after the injection, bone marrow cells were isolated from mice and cultured according to the procedure described in Worthington et al., (1985) and Rosenthal et al. (1987) with minor modifications. The cell suspension was adjusted to a density of about 6×10$^5$ cells/ml in MEM alpha medium (α-MEM, Gibco) containing 1% (v/v) bovine serum albumin (BSA, Sigma-Aldrich), 7.5 μM of 2-mercaptoethanol (Sigma-Aldrich), 1.4 mM of L-glutamine (Sigma-Aldrich), 10 μM of ferric chloride ($FeCl_3$, Sigma-Aldrich) and 50 mU/ml of EPO (Recormon Epoetin, Roche). The cells were plated at approximately 1.5×10$^5$ cells/well in 96-well plates (Costar), and cultured in a humidified 37° C. incubator containing 5% $CO_2$-95% air.

In the next day, different concentrations of compound A (0, 0.1, 0.5, 2.5, 12.5 and 20 μg/ml) were added to the cells, respectively, and incubated for 4 days. The relative levels of hemoglobin were determined using DAF-based hemoglobin colorimetry assay according to Kaiho (1985) and Worthington (1985) with minor modifications. In brief, cells were washed with PBS and lysed in Nonidet™ P 40 (NP-40, Sigma-Aldrich) (0.01% (v/v), 50 μl/well). Cells were then incubated with 4,5-diaminofluorescein (DAF, Sigma-Aldrich) (100 μg/ml, 100 μl/well), and 30% hydrogen peroxide (Sigma-Aldrich) (6 μl/well) for 5~10 min. The absorbance at 610 nm was measured by Victor 2 1420 Multilable Counter (Wallac, PerkinElmer). Results were expressed as relative index±S.E. (n=6). Statistical significance was evaluated by Student's t test (**P<0.01 versus control group (0 μg/ml)). It was found that compound A at concentrations between about 0.1 to about 20 μg/ml significantly enhanced hemoglobin formation (FIG. 1).

Example 3

Compound A Activates Erythroid Progenitor Cells in Cell Culture

To investigate the effect of "Compound A" on erythroid progenitor cells, burst-forming-units-erythroid (BFU-E) assay was conducted according to the procedures described in Corazza et al. (2004) and Jin et al. (2003) with modifications. Briefly, 6-week-old C57BL/6JNarl mice were purchased from the National Laboratory Animal Center (NLAC, Taiwan). Bone marrow cells were isolated from the mice, and the cell suspension was adjusted to about 8.3×10$^4$ cells/ml in α-MEM containing 15% (v/v) FBS (Gibco), 1% (v/v) BSA (Sigma-Aldrich), 0.8% (w/v) methylcellulose (Sigma-Aldrich), 10 μM 2-mercaptoethanol (Sigma-Aldrich), 2 U/ml Epo (Recormon Epoetin, Roche), and 10 ng/ml IL-3 (Sigma-Aldrich). Cells were plated at approximately 7.5×10$^4$ cells/well in 24-well plates (Falcon). They were incubated with different concentrations of Compound A (0, 0.1, 0.5, 2.5 and 12.5 μg/ml), respectively, for 9 days in a humidified 37° C. incubator containing 5% $CO_2$-95% air. The colonies were stained with 3-(4,5-dimethylthiazol-2-yl)-2,5-diphenyl-tetrazolium bromide (50 m/50 μl/well)

Figure 2:
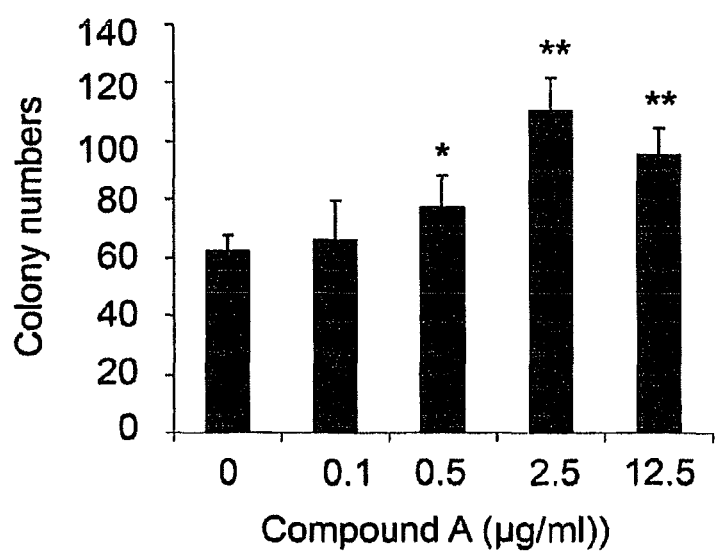
FIG. 2 is a graph showing Compound A stimulates erythroid progenitor cell proliferation using burst-forming units-erythroid (BFU-E) assay on bone marrow cells.

(MTT; Sigma-Aldrich). Plates were photographed while colonies of more than 50 cells were counted. Results were expressed as mean±S.E. (n=3). Statistical significance was evaluated by Student's t test (*P<0.05 and **P<0.01 versus control group (i.e., 0 concentration)). Compound A at concentrations of 0.5~12.5 µg/ml significantly increased the number of BFU-E colonies of bone marrow cells (FIG. 2). The results indicated that Compound A enhanced erythropoiesis by increasing hemoglobin formation and activating erythroid progenitor cells.

Example 4

Compound A Enhances Kidney Expression of Epo

C57BL/6JNarl mice, 8-10 weeks of age, were purchased from the National Laboratory Animal Center (NLAC, Taiwan). The kidney slices of mice were prepared as previously described with modifications (Parrish et al., 1995, Obatomi et al., 1998 and De Kanter et al., 1999). Briefly, mice were sacrificed by cervical dislocation and the kidneys were excised and immediately kept in gassed (95% $O_2$ and 5% $CO_2$) ice-cold sterile Krebs-HEPES buffer (pH 7.4) containing 20 mM HEPES (USB), 128 mM sodium chloride (Sigma-Aldrich), 2.5 mM potassium chloride (Sigma-Aldrich), 2.7 mM calcium chloride (Sigma-Aldrich), 1 mM magnesium chloride (Sigma-Aldrich) and 16 mM D-glucose (Sigma-Aldrich). The kidneys were decapsulated and cored perpendicular to the cortico-papillary axis. Kidney slices (250 µm) were prepared in microslicer (D.S.K microslicer, DRK 1000, Dosaka EM Co) filled with gassed (95% $O_2$: 5% $CO_2$) ice-cold sterile Krebs-HEPES buffer. Kidney slices were collected and stored on ice in gassed (95% $O_2$, 5% $CO_2$) ice-cold sterile Krebs-HEPES buffer and used within 10 min of slice preparations.

Figure 3:
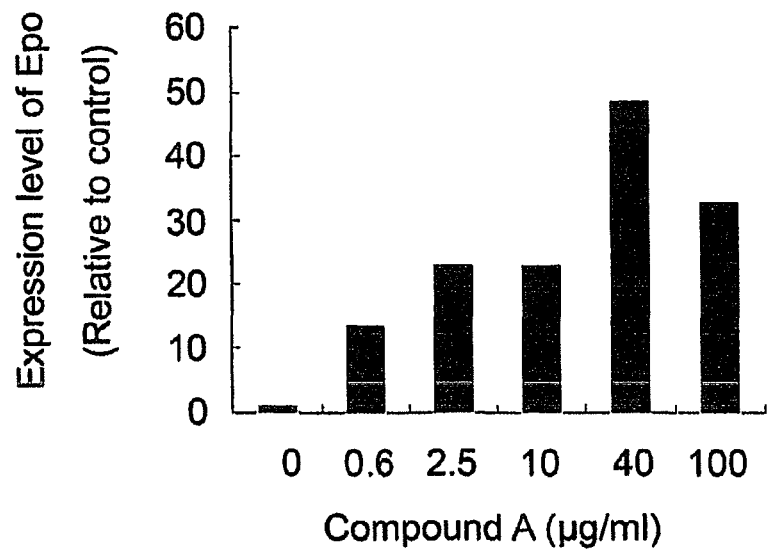
FIG. 3 is a graph showing Compound A increases the expression of erythropoietin (Epo) in kidney tissue.

Kidney slices were preincubated in a 24-well plate (Falcon) containing 1.0 ml/well of gassed (95% $O_2$, 5% $CO_2$) fresh media (DMEM/F12 (Gibco/Invitrogen) containing 15 mM HEPES (USB), 20 mM sodium bicarbonate (Sigma-Aldrich)) and 5% (v/v) FBS (Gibco) for 90~120 min at 37° C. in a 95% $O_2$: 5% $CO_2$ atmosphere chamber. Afterwards, kidney slices were incubated with different concentrations of Compound A (0, 0.6, 2.5, 10, 40 and 100 µg/ml), respectively, for 16 hr at 37° C. in a 50% $O_2$: 5% $CO_2$: 45% $N_2$ atmosphere chamber. Ribonucleic acids (RNA) of kidney slices were extracted by RNA-Bee™ RNA isolation solvent (Tel-test). Total RNA (5 µg) was used to prepare complementary deoxyribonucleic acid (cDNA) using MMLV reverse transcriptase (Promega). The reverse-transcribed cDNA samples were analyzed by polymerase chain reaction (PCR) using ABI GeneAmp™ system 2700 (Applied Biosystems) with primers targeting toward mouse β-actin (SEQ ID NOs: 1 and 2) and erythropoietin (Epo) (SEQ ID NOs: 3 and 4) (Table 1). Results were compared with control group (0 µg/ml) and expressed as relative index. The results indicated that Compound A increased the expression of Epo in kidney tissue (FIG. 3).

TABLE 1

| Primer | Sequence | ID NO. |
| --- | --- | --- |
| β-actin-F | GTGGGCCGCCCTAGGCACCA | SEQ ID NO: 1 |
| β-actin-R | TGGCCTTAGGGTTCAGGGGG | SEQ ID NO: 2 |
| Epo-F | AATGGAGGTGGAAGAACAGG | SEQ ID NO: 3 |

TABLE 1-continued

| Primer | Sequence | ID NO. |
| --- | --- | --- |
| Epo-R | ACCCGAAGCAGTGAAGTGA | SEQ ID NO: 4 |
| GAPDH-F | TGGCATCGTGGAAGGGCTCA | SEQ ID NO: 5 |
| GAPDH-R | GGAAGAATGGGAGTTGCTGT | SEQ ID NO: 6 |
| HGF-F | CTTGGCATCCACGATGTTCAT | SEQ ID NO: 7 |
| HGF-R | TGGTGCTGACTGCATTTCTCA | SEQ ID NO: 8 |

Example 5

Compound A Enhances Liver Expression of Epo

C57BL/6JNarl mice, 8-10 weeks of age, were purchased from the National Laboratory Animal Center (NLAC, Taiwan). The hepatocytes were isolated as previously described with modifications (Kreamer et al., 1986). Briefly, mice were anaesthetized with Avertin (2% (w/v) 2,2,2-tribromoethanol, i.p., 300 mg/Kg body weight) and the liver was perfused in situ through portal vein with a calcium-free Hank's balanced salt solution (HBSS) containing 0.5 mM Ethylene glycol-bis(2-aminoethylether)-N,N,N',N'-tetraacetic acid (EGTA; Sigma-Aldrich). The flow rate was 1 ml/min with the perfusate exiting via the severed inferior vena cava. After 10 min of perfusion, HBSS containing 0.05% (w/v) collagenase (Type II; Worthington Biochemical Corporation) and 1 mM calcium chloride (Sigma-Aldrich) was introduced into the perfusion apparatus. The perfusion was continued for another 10 min at the same flow rate. The partially digested liver was removed, placed in a 60-mm culture dish (BD Falcon) containing HBSS, and gently minced to open the liver capsule. The minced liver suspension was filtered through a nylon mesh (about 300 µm pore size), centrifuged at 50×g for 3 min to obtain a cell pellet. The percoll (GE Healthcare) medium of a density of 1.06 g/ml was prepared. The cell pellet was suspended in DMEM medium (Gibco/Invitrogen), centrifuged with the percoll medium at 50×g for 10 min at 4° C., washed once with DMEM medium and followed by centrifugation at 50×g for 2 min to obtain hepatocytes.

Figure 4:
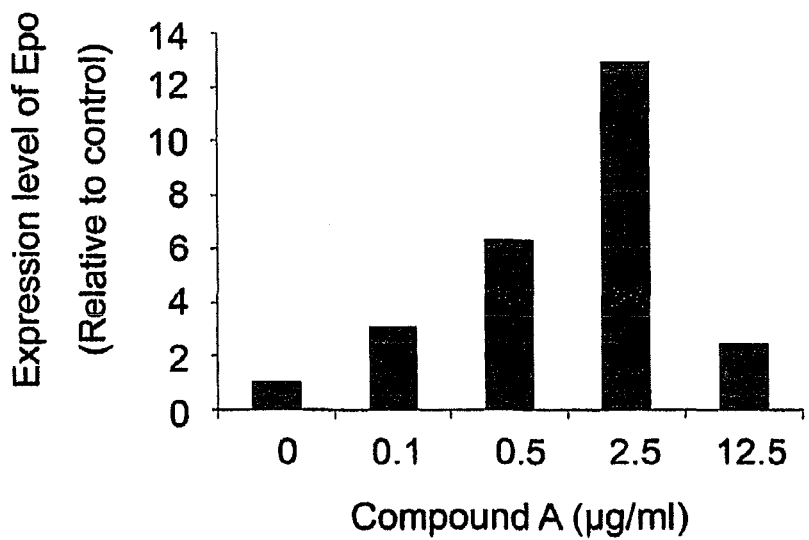
FIG. 4 is a graph showing Compound A increases the expression of erythropoietin (Epo) in hepatocytes.

The isolated hepatocytes were plated in 6-well plates (Costar) at approximately 6×10$^5$ cells/well in DMEM medium (Gibco/Invitrogen) containing 10% FBS (Gibco) in a humidified 37° C. incubator containing 5% $CO_2$-95% air. After 3 hr, the medium was removed, and the cells were incubated with different concentrations of compound A (0, 0.1, 0.5, 2.5 and 12.5 µg/ml), respectively, for 24 hours. The RNA of hepatocyte was extracted by RNA-Bee™ RNA isolation solvent (Tel-test) for reverse transcription, and the transcripts analyzed by PCR as previously described. The results indicated that Compound A enhanced the expression of Epo in hepatocytes (FIG. 4).

Example 6

Compound A Enhances Kidney Function in a Cisplatin-Induced Acute Renal Failure Animal Model The effects of Compound A treatment on cisplatin-induced acute renal failure animal model were investigated. C57BL/6JNarl mice (8-week-old) were purchased from the National Laboratory Animal Center (NLAC, Taiwan). Cisplatin (Sigma-Aldrich) was dissolved in normal saline (0.9% (w/v) sodium chloride, Sigma-Aldrich) at a concentration of 1 mg/ml, and injected into mice intraperitoneally (i.p.) according to the following schedule: day 1, 7 mg/kg; day 5, 6 mg/kg; and day 9, 6 mg/kg. For cisplatin-untreated normal mice group, normal saline injections of corresponding volumes were given i.p. in parallel. At day 13, serum samples were collected and blood urea nitrogen (BUN) contents were assayed. Cisplatin-injected mice with BUN levels more than 100 mg/dl and the cisplatin-untreated normal mice were further divided into 5 groups, 6 mice per group, for feeding with Compound A for 2 weeks: (1) Normal group: Mice were injected with normal saline and followed by feeding with a standard diet; (2) Control group: Mice were injected with cisplatin and followed by feeding with a standard diet; (3) Pomu 10 mg/kg/day group: Mice were injected with cisplatin and followed by feeding with Compound A at the dose of 10 mg/kg/day; (4) Pomu 30 mg/kg/day group: Mice were injected with cisplatin and followed by Compound A at the dose of 30 mg/kg/day; (5) Pomu 90 mg/kg/day group: Mice were injected with cisplatin and followed by Compound A treatment at the dose of 90 mg/kg/day.

Figure 5:
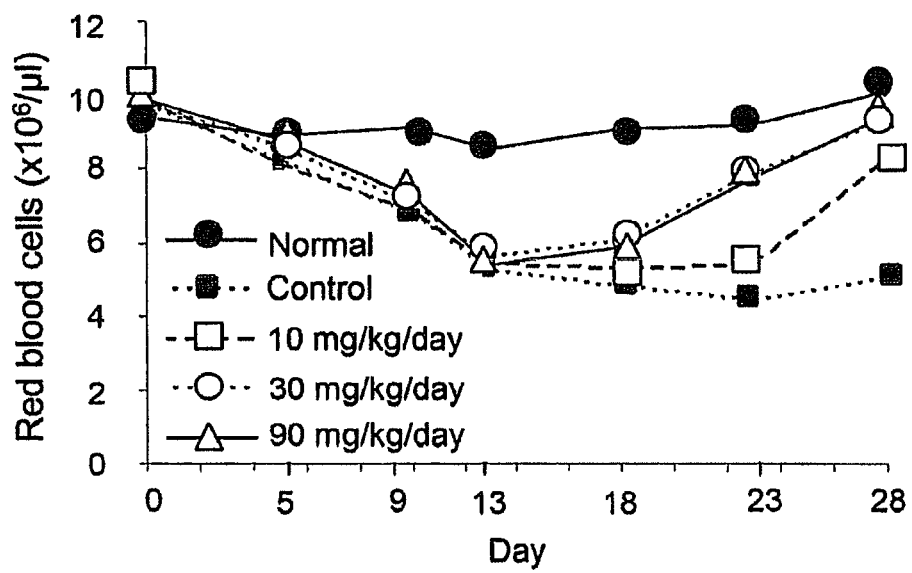
FIG. 5 is a graph showing Compound A increases the number of red blood cells in a cisplatin-induced acute renal failure animal model.
Figure 6:
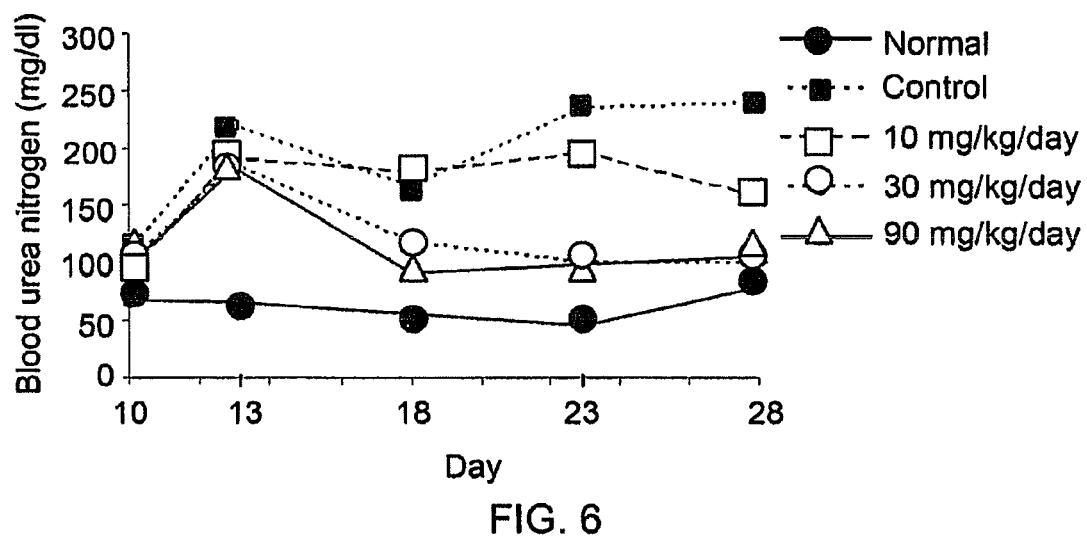
FIG. 6 is a graph showing Compound A decreases serum blood urea nitrogen levels in a cisplatin-induced acute renal failure animal model.
Figure 7:
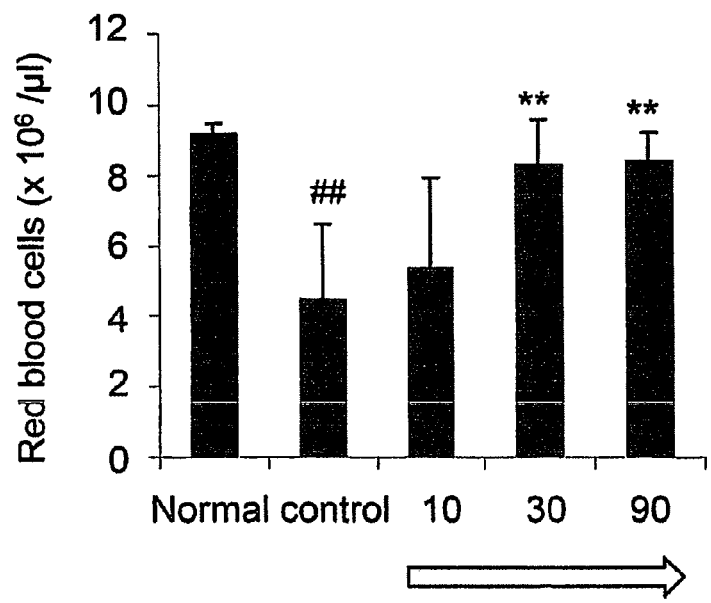
FIG. 7 is a graph showing Compound A increases the number of red blood cells in a cisplatin-induced acute renal failure animal model at day 23. The horizontal arrow represents Compound A treatment (mg/Kg/day).
Figure 8:
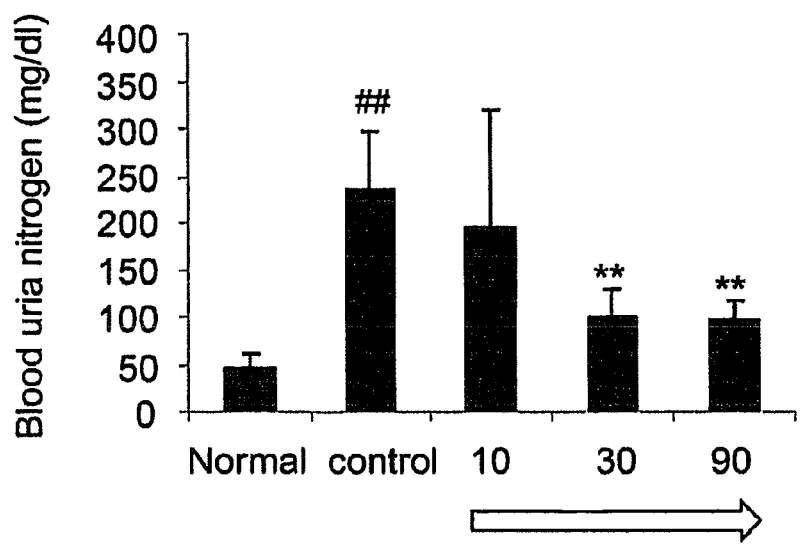
FIG. 8 is a graph showing Compound A decreases serum blood urea nitrogen levels in a cisplatin-induced acute renal failure animal model at day 23. The horizontal arrow represents Compound A treatment (mg/Kg/day).

Blood samples were collected from the retro-orbital sinus of mice at day 0, 5, 10, 13, 18, 23 and 28. Red blood cell (RBC) concentrations were determined by complete blood cell count using Sysmex® Kx-21 hematology analyzer. Blood urea nitrogen (BUN) levels were determined by urease GLDH method (Urea FS, DiaSys). Results were expressed as mean±S.E. (n=5~6). Statistical significance was evaluated by Student's t test (##P<0.01 versus normal group and **P<0.01 versus control group). The results indicated that Compound A treatment at concentrations of 30~90 mg/kg/day increased the number of red blood cells (RBCs) (FIG. 5) and decreased serum BUN levels (FIG. 6). At day 23, Compound A at concentrations between 30~90 mg/kg/day significantly increased the number of RBCs (FIG. 7) while decreasing serum BUN levels (FIG. 8). The horizontal arrow in FIGS. 7 and 8 represents Compound A treatment (mg/Kg/day). The data indicated that the Compound A treatment enhanced renal functions and reduced anemia in a cisplatin-induced acute renal failure animal model. The results were in agreement with the ability of the Compound A in enhancing erythropoiesis.

Example 7

Compound A Increases Liver Expressions of Epo and Hepatocyte Growth Factor in a Cisplatin-Induced Acute Renal Failure Animal Model At the end of the experiments described in EXAMPLE 6 (i.e., day 28), mice were sacrificed, kidney and liver tissues were removed, and bone marrow cells were isolated. RNA from tissues and bone marrow cells were extracted by RNA-Bee™ RNA isolation solvent (Tel-test). Total RNA (5 µg) was used to prepare cDNA using MMLV reverse transcriptase (Promega). The reverse-transcribed cDNA samples were analyzed by PCR using ABI GeneAmp™ system 2700 (Applied Biosystems) and the SYBR Green Master Mix kit (Applied Biosystems) using primers targeting toward mouse glyceraldehyde 3-phosphate dehydrogenase (GAPDH) (SEQ ID NOs: 5 and 6), erythropoietin (Epo) (SEQ ID NOs: 3 and 4) and hepatocyte growth factor (HGF) (SEQ ID NOs: 7 and 8) (Table 1). Results were expressed as relative index±S.E. (n=5~6). Statistical significance was evaluated by Student's t test (## P<0.01 versus normal group and *P<0.05, **P<0.01 versus control group).

Figure 9:
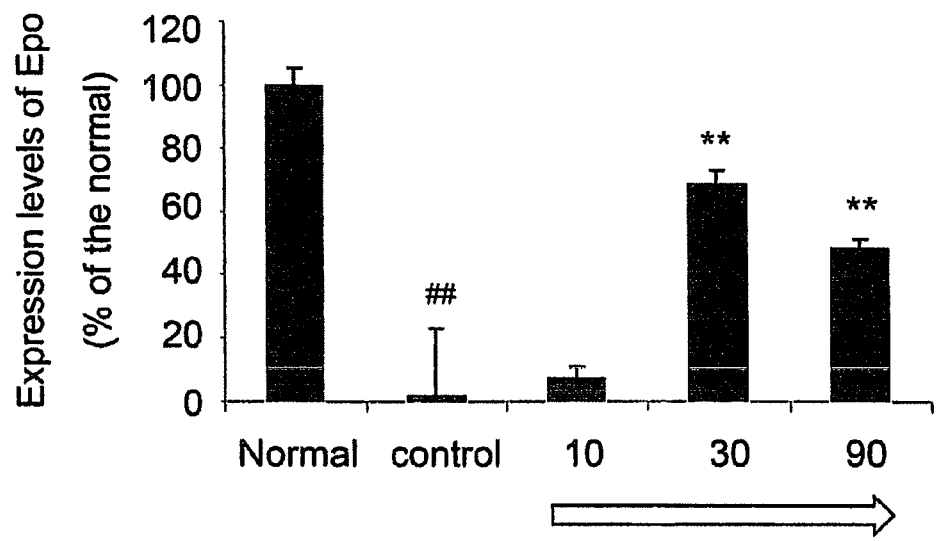
FIG. 9 is a graph showing Compound A increases the expression of erythropoietin (Epo) in liver tissue in a cisplatin-induced acute renal failure animal model. The horizontal arrow represents Compound A treatment (mg/Kg/day).
Figure 10:
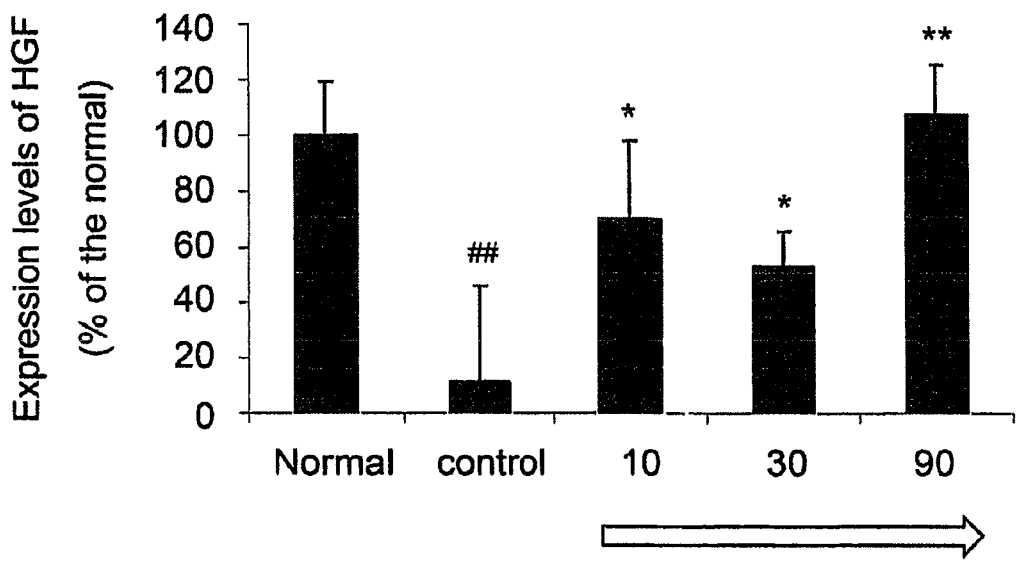
FIG. 10 is a graph showing Compound A increases the expression of hepatocyte growth factor (HGF) in liver tissue in a cisplatin-induced acute renal failure animal model. The horizontal arrow represents Compound A treatment (mg/Kg/day).

The results indicated that Compound A at concentrations of 30~90 mg/kg/day significantly increased the expression of Epo in liver in a cisplatin-induced acute renal failure animal model as compared to the untreated control group (FIG. 9). Livers and kidneys are two major organs that make Epo. Compound A was found to enhance the expression of Epo in kidney tissue (FIG. 3), hepatocytes (FIG. 4) and liver tissue (FIG. 10). Moreover, compound A (10~90 mg/Kg/day) treatment also enhanced the expression of HGF in liver tissue (FIG. 10). The horizontal arrow in FIGS. 9 and 10 represents Compound A treatment (mg/Kg/day).

Example 8

Figure 11:
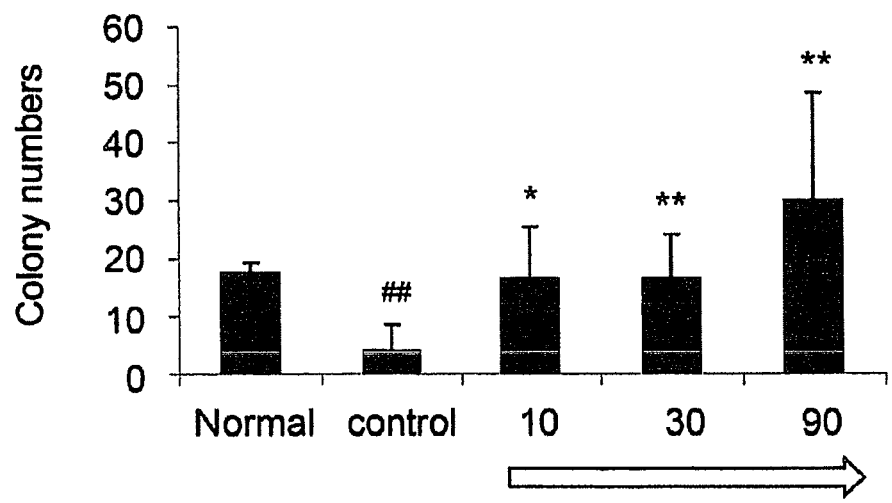
FIG. 11 is a graph showing Compound A stimulates erythroid progenitor cell proliferation using burst-forming units-erythroid (BFU-E) assay on bone marrow cells in a cisplatin-induced acute renal failure animal model. The horizontal arrow represents Compound A treatment (mg/Kg/day).

Compound A Activates Erythroid Progenitor Cells in a Cisplatin-Induced Acute Renal Failure Animal Model The isolated bone marrow cells described in EXAMPLE 7 were cultured for 12 days in a humidified 37° C. incubator containing 5% $CO_2$-95% air for burst-forming-units-erythroid (BFU-E) assay as described above. Results were expressed as relative index±S.E. (n=5~6). Statistical significance was evaluated by Student's t test (## P<0.01 versus normal group and *P<0.05, **P<0.01 versus control group). It was found that Compound A at concentrations of 10~90 mg/kg/day significantly increased the number of BFU-E colonies of bone marrow cells (FIG. 11). The horizontal arrow in FIG. 11 represents Compound A treatment (mg/Kg/day). The results indicated that Compound A activated erythroid progenitor cells and enhanced erythropoiesis.

The compound 2,3,5,4'-tetrahydroxystilbene 2-O-β-D-glucopyranoside, i.e., Compound A, has been found in several plants. According to the literatures, Compound A has the following pharmacological effects: stimulating melanogenesis by activating tyrosinase (Guan et al., 2008), inhibiting lipid peroxidation (Kimura et al., 1983), having a protective effect on colitis through alleviating oxygen and nitrogen free radicals level and down-regulating inducible nitric oxide synthase expression (Wang et al., 2008), having anti-atherosclerosis effect via its antagonistic effects on oxidation of lipoprotein, proliferation and decrease in nitric oxide content of coronary arterial smooth cells (Liu et al., 2007), having anti-inflammatory function that is related to the inhibition of cyclooxygenase-2 enzyme activity and expression (Zhang et al., 2007), and are beneficial for Alzheimer disease and cognitive impairment (Wang et al., 2007).

U.S. Publication No. 20050042314 (entitled "Extracts of *Polygonum multiflorum* Thunb., and preparation process and uses of the same) discloses that extract products from the root of *Polygonum multiflorum* Thunb. are biologically active in increasing proliferation, growth and/or differentiation of hematocytes and bone marrow cells. The Fleeceflower root contains numerous chemical components, such as emodin, chrysophanol, physcion, rhein, chrysophanol anthrone, resveratrol, piceid, 2,3,5,4'-tetrahydroxystilbene-2-O-β-D-glucopyranoside, 2,3,5,4'-tetrahydroxystilbene-2-O-β-D-gluco-pyranoside-2"-O-mo-nogalloyl ester, 2,3,5,4'-tetrahydroxystilbene-2-O-β-D-glucopyranosid-e-3"-O-monogalloyl ester, gallic acid, catechin, epicatechin, 3-O-galloyl(−)-catechin, and 3-O-galloyl(−)epicatechin, 3-O-galloyl-procyanidin B-2,3,3'-di-0-galloyl-procyanidin B-2, and .beta.-sitosterol. The U.S. Publication No. 20050042314 is silent as to which chemical component(s) is active.

As described above, Compound A has been proved to be biologically active in increasing Epo production and enhancing erythropoiesis and kidney functions. The glucosyl group in Compound A may be replaced by saccharides such as dihydroxyacetone, galactose, glyceraldehydes, threose, xylose, mannose, ribose, ribulose, xylulose, tagatose, psicose (allulose), fructose, sorbose, rhamnose, erythrose, erythrulose, arabinose, lyxose, allose, altrose, gulose, idose, talose, and any combinations thereof.

It is well known that Epo stimulates erythropoiesis, and that Epo is required for erythropoiesis (Moritz et al., 1997). It has also been reported that Epo has renoprotective effects (Sepodes et al., 2006 and Arcasoy, 2008). In addition to increasing Epo production, Compound A enhances erythropoiesis and kidney functions.

HGF is a multifunctional cytokine that is related to cell survival, growth, motility and morphogenesis, tissue regeneration, protection and repair. It has been reported that HGF activates signal transduction from Epo receptor (Iguchi et al., 1999 and Isobe et al., 2006). HGF has been shown to have therapeutic potential for allergic inflammation (Ito et al., 2008), osteoarthritis, rheumatoid arthritis, muscular dystrophy, muscular atrophy, skin ulcer, burn, scleroderma, crush syndrome (Funakoshi and Nakamura, 2003), cerebrovascular diseases such as transient ischemic attack and stroke, neurodegenerative diseases such as amyotrophic lateral sclerosis, Alzheimer's disease and Parkinson's disease, spinal cord injury, diabetic retinopathy, peripheral neuropathy, spinal canal stenosis, deafness (Funakoshi and Nakamura, 2003 and Takeo et al., 2007), acute hepatitis, liver cirrhosis, fulminant hepatitis, fatty liver, surgical treatments for liver transplantation, partial resection and ischemia (Funakoshi and Nakamura, 2003 and Mizuno and Nakamura, 2007), kidney fibrosis, acute renal failure, chronic renal failure such as nephritic syndrome and obstructive nephropathy, surgical treatments for renal transplantation and ischemia, diabetic nephropathy (Matsumoto and Nakamura, 2001; Funakoshi and Nakamura, 2003 and Liu, 2004), acute pneumonia, pulmonary fibrosis, surgical treatments for lung transplantation, partial resection and ischemia (Funakoshi and Nakamura, 2003), inflammation-mediated heart diseases such as cardiac allograft rejection and myocarditis, cardiovascular diseases such as angina, cardiac infarction, cardiomyopathy and atherosclerosis obliterans (Funakoshi and Nakamura, 2003 and Isobe et al., 2006), intestinal mucosal injury, inflammatory bowel disease (Ido et al., 2005), gastric ulcer and diabetes mellitus (Funakoshi and Nakamura, 2003).

Compound A has a structure based on 3,4',5-trihydroxy-trans-stilbene, which is a natural compound possessing numerous biological activities, including renoprotection via nitric oxide dependent and/or antioxidant mechanisms (Sharma et al., 2006; Shankar et al., 2007; Do Amaral et al., 2008 and Orallo, 2008). Compound A was found to be superior to 3,4',5-trihydroxy-trans-stilbene in enhancing renal functions and improving anemia (data not shown).

rHuEpo and NESP have been used in intravenous (i.v.) or subcutaneous (s.c.) injection for treating anemia of CKD, anemia in cancer patients receiving chemotherapy, anemia in zidovudine-treated patients infected with human immunodeficiency virus (Fisher, 2003). It has been recommended that the administration be given more than once per week for maintenance therapy. The cost, the inconvenience due to frequent injections (parenteral administration) and development of anti-Epo antibodies due to inherent antigenicity of rHuEpo all point to a need for developing an improved therapeutic agent. Oral administration of Compound A, one of 3,4',5-trihydroxy-trans-stilbene analogs, can increase Epo formation, enhances erythropoiesis and kidney functions, and reduces anemia.

The compound 3,4',5-trihydroxy-trans-stilbene has been reported to have renoprotective effects via nitric oxide dependent and/or antioxidant mechanisms. Compound A is superior to 3,4',5-trihydroxy-trans-stilbene in enhancing erythropoiesis and kidney functions. Moreover, Compound A has the advantages that recombinant Epo does not have: An oral administration of Compound A does not pose inherent antigenicity, which recombinant Epo has. In addition, the route of administration of rEPO is inconvenient because it requires frequent injections. Compound A may be beneficial for disorder-associated anemia, such as CKD, cancer, acute and chronic infections, autoimmune, inflammation, chronic rejection after solid-organ transplantation, chemotherapy-induced anemia, and tissue ischemia.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

LIST OF REFERENCES

Arcasoy M O. 2008. Br J Haematol. 141:14-31.
Bunn H F. 2007. Blood. 109:868-873.
Corazza F. et al. 2004. Pediatr Res. 55:152-158.
De Kanter R. et al. 1999. Toxicol in Vitro. 13:737-744.
Do Amaral C L. et al. 2008. Arch Toxicol. 82:363-730.
Eckardt K U and Kurtz A. 1992. Eur J Clin Invest. 89:753-760.
Eckardt K U and Kurtz A. 2005. Eur J Clin Invest. 35 Suppl 3:13-19.
Fisher J W. 2003. Exp Biol Med (Maywood). 228:1-14.
Funakoshi H and Nakamura T. 2003. Clin Chim Acta. 327:1-23.
Guan S. et al. 2008. Phytother Res. 22:660-663.
Hodges V M. et al. 2007. Crit Rev Oncol Hematol. 64:139-158.
Ido A. 2005. J Gastroenterol. 40:925-931.
Iguchi T. et al. 1999. Stem Cells. 17:82-91.
Isobe M. et al. 2006. Trends Cardiovasc Med. 16:188-193.

Ito W. et al. 2008. Int Arch Allergy Immunol. 146 Suppl 1:82-87.
Jin M. et al. 2003. Exp Biol Med (Maywood). 228:759-766.
Kaiho S and Mizuno K. 1985. Anal Biochem. 149:117-120.
Kimura Y. et al. 1983. Planta Med. 49:51-54.
Kreamer B L. et al. 1986. In Vitro Cell Dev Biol. 22:201-211.
Levey A S. et al. 2005. Kidney Int. 67:2089-3100.
Liu Q L. et al. 2007. J Asian Nat Prod Res. 9:689-697.
Liu Y. 2004. Am J Physiol Renal Physiol. 287:F7-16.
Matsumoto K and Nakamura T. 2001. Kidney Int. 59:2023-2038.
Mizuno S and Nakamura T. 2007. Regen Med. 2:161-170.
Moritz K M. et al. 1997. Am J Physiol. 273:R1829-1844.
Obatomi D K. et al. 1998. Toxicol in Vitro. 12:725-737.
Orallo F. 2008. Curr Med Chem. 15:1887-1898.
Parrish A R. et al. 1995. Life Sci. 57:1887-1901.
Paschos N. 2008. Int J Biol Sci. 4:161-168.
Rosenthal A. et al. 1987. Exp Hematol. 13:174-184.
Sepodes B. et al. 2006. Transpl Int. 19:919-926.
Shankar S. et al. 2007. Front Biosci. 12:4839-4854.
Sharma S. et al. 2006. Pharmacology. 76:69-75.
Takeo et al. 2007. Yakugaku Zasshi. 127:1813-1823.
Wang R. et al. 2007. Neuroscience. 149:739-746.
Wang X. et al. 2008. Eur J Pharmacol. 578:339-348.
Weiss G and Goodnough L T. 2005. N Engl J Med. 352:1011-1023.
Wish J B and Coyne D W. 2007. Mayo Clin Proc. 82:1371-1380.
Worthington R E. et al. 1987. Exp Hematol. 15:85-92.
Zarzecki M. et al. 2004. Pol Arch Med Wewn. 112:1211-1219.
Zhang Y Z. et al. 2007. J Asian Nat Prod Res. 9:355-363.

What is claimed is:

1. A method for treating anemia in a subject in need thereof, comprising administering to the subject a pharmaceutical composition consisting essentially of an effective amount of a compound of Formula I:

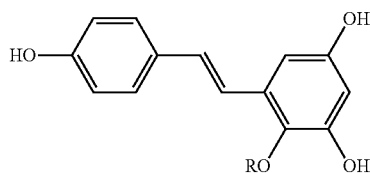

(I) wherein R is a glycosyl group,
wherein the compound of Formula I is administered as a sole active ingredient.

2. A method for treating cardiomyopathy in a subject in need thereof, comprising administering to the subject a pharmaceutical composition consisting essentially of an effective amount of a compound of Formula I:

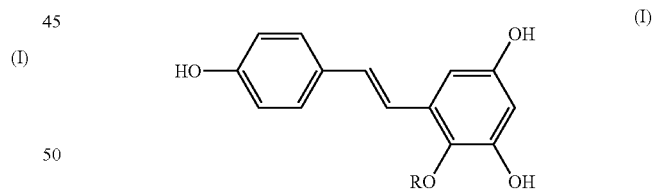

wherein R is a glycosyl group, wherein the compound of Formula I is administered as an active ingredient.

3. The method of claim 2, wherein the compound of Formula I is administered as a sole active ingredient.

* * * * *

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Forward primer for beta-actin

<400> SEQUENCE: 1
gtgggccgcc ctaggcacca                                                      20

<210> SEQ ID NO 2
<211> LENGTH: 20
<212> TYPE: DNA
<213> ORGANISM: Artificial Sequence
<220> FEATURE:
<223> OTHER INFORMATION: Reverse primer for beta-actin

<400> SEQUENCE: 2
tggccttagg gttcaggggg                                                      20

<210> SEQ ID NO 3
<211> LENGTH: 20
<212> TYPE: DNA
<213> ORGANISM: Artificial Sequence
<220> FEATURE:
<223> OTHER INFORMATION: Forward primer for erythropoietin (Epo)

<400> SEQUENCE: 3
aatggaggtg gaagaacagg                                                      20

<210> SEQ ID NO 4
<211> LENGTH: 19
<212> TYPE: DNA
<213> ORGANISM: Artificial Sequence
<220> FEATURE:
<223> OTHER INFORMATION: Reverse primer for Epo

<400> SEQUENCE: 4
acccgaagca gtgaagtga                                                       19

<210> SEQ ID NO 5
<211> LENGTH: 20
<212> TYPE: DNA
<213> ORGANISM: Artificial Sequence
<220> FEATURE:
<223> OTHER INFORMATION: Forward primer for glyceraldehyde 3-phosphate
```

```
                dehydrogenase (GAPDH)

<400> SEQUENCE: 5
tggcatcgtg gaagggctca                                              20

<210> SEQ ID NO 6
<211> LENGTH: 20
<212> TYPE: DNA
<213> ORGANISM: Artificial Sequence
<220> FEATURE:
<223> OTHER INFORMATION: Reverse primer for GAPDH

<400> SEQUENCE: 6
ggaagaatgg gagttgctgt                                              20

<210> SEQ ID NO 7
<211> LENGTH: 21
<212> TYPE: DNA
<213> ORGANISM: Artificial Sequence
<220> FEATURE:
<223> OTHER INFORMATION: Forward primer for hepatocyte growth factor
      (HGF)

<400> SEQUENCE: 7
cttggcatcc acgatgttca t                                            21

<210> SEQ ID NO 8
<211> LENGTH: 21
<212> TYPE: DNA
<213> ORGANISM: Artificial Sequence
<220> FEATURE:
<223> OTHER INFORMATION: Reverse primer for HGF

<400> SEQUENCE: 8
tggtgctgac tgcatttctc a                                            21
```